United States Patent [19]

Gezari

[11] 4,212,298
[45] Jul. 15, 1980

[54] THERMODILUTION INJECTOR

[75] Inventor: Walter A. Gezari, Killingworth, Conn.

[73] Assignee: Hart Associates, Inc., East Hartford, Conn.

[21] Appl. No.: 843,333

[22] Filed: Oct. 20, 1977

Related U.S. Application Data

[63] Continuation-in-part of Ser. No. 735,340, Oct. 26, 1976, abandoned.

[51] Int. Cl.² ............................................. A61M 5/00
[52] U.S. Cl. ................................ 128/215; 128/218 A; 128/DIG. 12
[58] Field of Search ........... 128/218 A, 218 P, 218 R, 128/214 E, 214 F, 1.1, 215, DIG. 12, DIG. 13, 173 H, 224, 225; 250/505, 506, 515

[56] References Cited

U.S. PATENT DOCUMENTS

| | | | |
|---|---|---|---|
| 3,515,130 | 6/1970 | Tsujino | 128/173 H |
| 3,561,443 | 2/1971 | Banker | 128/173 H |
| 3,674,009 | 7/1972 | Williamson | 128/1.1 X |
| 3,683,183 | 8/1972 | Vizzini et al. | 128/1.1 X |
| 3,731,669 | 5/1973 | Fitzgerald | 128/1.1 X |
| 3,768,472 | 10/1973 | Hodosh et al. | 128/218 A X |
| 3,945,379 | 3/1976 | Pritz et al. | 128/173 H |

Primary Examiner—John D. Yasko
Attorney, Agent, or Firm—Fishman and Van Kirk

[57] ABSTRACT

A thermodilution injector is presented in which a pneumatically powered piston operates the plunger of a syringe to deliver a measured amount of injectate in an accurately predetermined time period.

23 Claims, 8 Drawing Figures

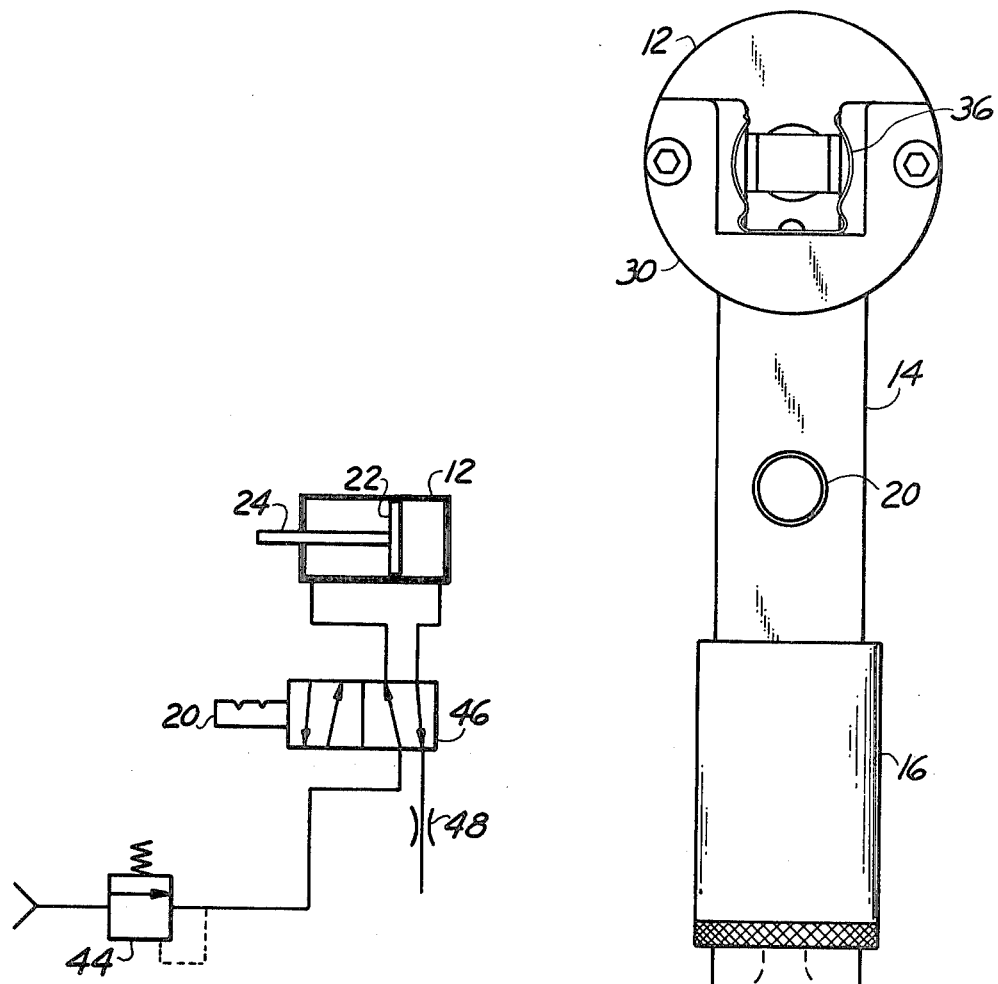

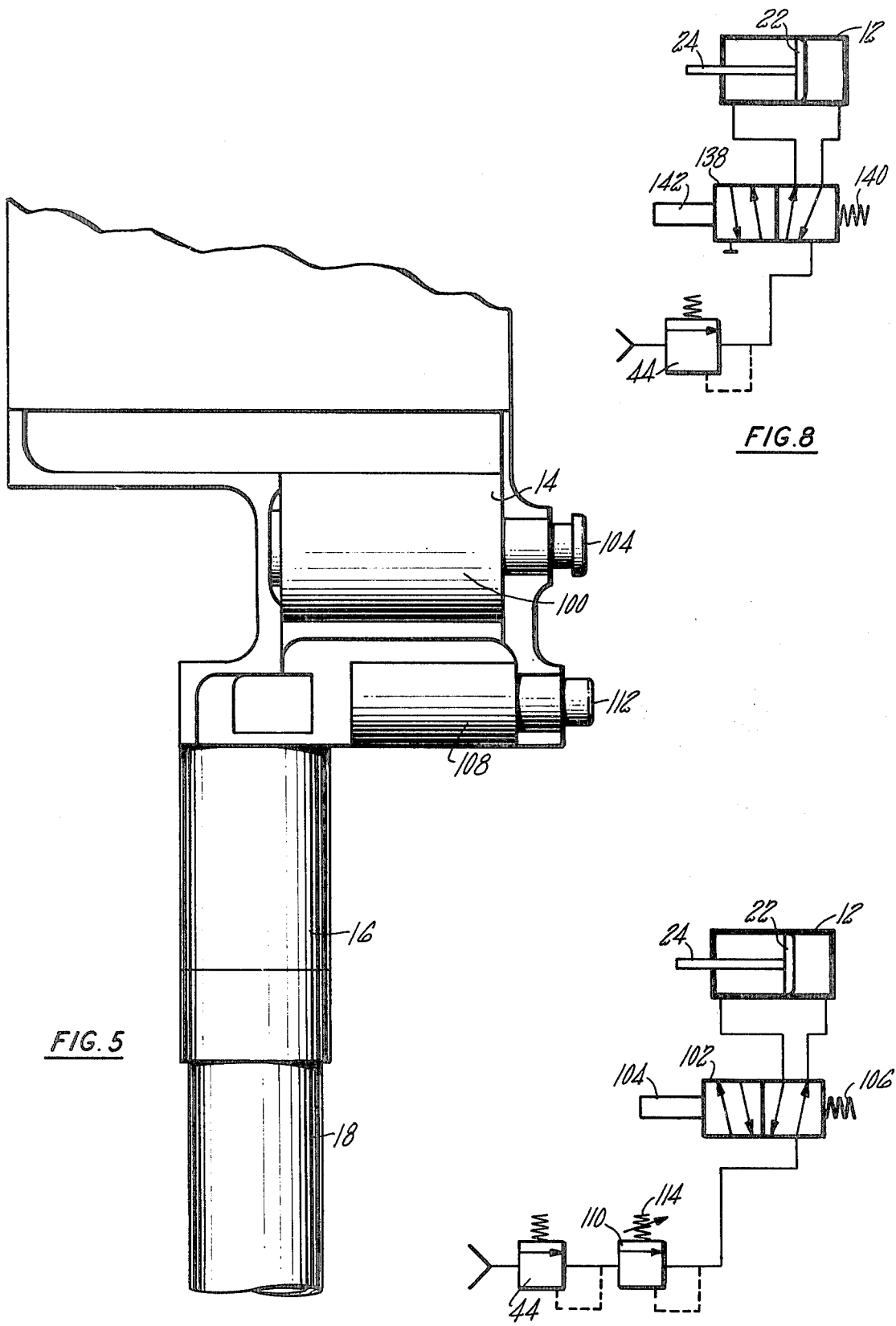

THERMODILUTION INJECTOR

CROSS-REFERENCE TO RELATED APPLICATIONS:

This application is a continuation-in-part of U.S. application Ser. No. 735,340 filed Oct. 26, 1976, now abandoned.

BACKGROUND OF THE INVENTION

A well known test for the determination of cardiac output involves the injection of a measured amount of cold injectate solution into the right heart proximal to the pulmonary artery in a predetermined time period of short duration, such as, on the order of two seconds. The temperature drop of the blood passing a thermistor positioned in the heart is then sensed and measured. The decrease in blood temperature in a given time resulting from the injectate solution, when integrated by a cardiac output computer, is a measure of the output capacity of the heart in liters per minute. This technique for determining cardiac output is well known and is of considerable importance in diagnosing and treating critically ill patients. The value of the technique of thermodilution cardiac output monitoring is directly related to the accuracy of the process. Many thermodilution cardiac output computers are commercially available for obtaining determinations of cardiac output from a blood temperature drop curve.

The reliability of the technique of thermodilution cardiac output monitoring depends on the accuracy and repeatability of the injection process. At the present time the greatest potential source of error is in the time period for the introduction of the injectate. In order for the output readings to be accurate, repeatable and reliable, the injectate must be delivered to the patient over a short predetermined time period, which time period must be the same for each injection. If the time period of injection varies, the rate of change of blood temperature over a given time will also vary, and the computer output readings will thus be rendered inaccurate and unreliable. Bearing in mind that injection should occur over a time period of approximately two seconds, the time it takes for 10 cc of O'dextrose to be injected manually, it can readily be seen that a variation of as little as a fraction of a second from injection to injection can lead to substantial errors in measurement.

In the present practice of the thermodilution injection technique, a doctor or medical technician manually operates a syringe to deliver the injectate into a catheter placed in the right heart proximal to the pulmonary artery. Manual introduction of the injectate has the potential for significant inaccuracies which in turn, lead to serious errors in the computer output. It is extremely difficult for a medical technician to deliver a steady flow of the injectate repeatably over the same time period, and it is even more difficult for different medical technicians to deliver the full amount of injectate in the identical time period repeatably. Thus, the delivery rate of the injectate usually varies, and the time period is usually somewhat greater or somewhat less than the time period for the previous injection. As a result large fluctuations of cardiac output are routinely observed in a series of determinations done on the same patient by different operators. The most probable cardiac output volume is arrived at by sampling several of the closest readings and rejecting the rest.

SUMMARY OF THE INVENTION

The problem of accuracy and repeatability of thermodilution injection is solved by the thermodilution injector of the present invention which accomplishes the delivery of an accurate amount of injectate at a predetermined rate and over a predetermined time period, with the rate and time period of injection being accurately determined and repeatable for all injections.

The present invention provides an accurate and reliable injector device to replace the manual injection technique heretofore used in the art. The injector device of the present invention includes a pneumatically powered piston which is connected to operate the plunger of a syringe. Fluid from a regulated pressure supply is delivered to the device to operate the piston in a stroke of repeatable time duration; the injection time being inversely proportional to secondary regulator pressure. The plunger of the syringe is thus depressed in an accurate time period so that the injectate in the syringe is delivered to the cardiac catheter in the desired time period.

Apparatus in accordance with the present invention may also include a detent control valve. The control valve causes retraction of the piston at a slower rate than the rate at which the piston was advanced, thereby providing for aspiration of the syringe for another injection.

Accordingly, one object of the present invention is to provide an accurate and reliable thermodilution injector for cardiac output monitoring.

Another object of the present invention is to provide a thermodilution injector for cardiac monitoring in which a measured amount of injectate is always delivered within an accurate predetermined time period.

Other objects and advantages of the present invention will be apparent to and understood by those skilled in the art from the following detailed description and drawings.

BRIEF DESCRIPTION OF THE DRAWING

Referring now to the drawings, wherein like elements are numbered alike in the several figures:

FIG. 3 is a front elevation view of the thermodilution injector of the present invention.

FIG. 4 is a schematic showing of the pneumatic circuit of the thermodilution injector of the present invention.

FIG. 5 is a partial view of a modified version of the thermodilution injector.

FIG. 6 is a schematic diagram of the pneumatic circuit for the modified version of FIG. 5.

FIG. 8 is a schematic of a pneumatic circuit for isotope injection.

DESCRIPTION OF THE PREFERRED EMBODIMENT

Figure 1:
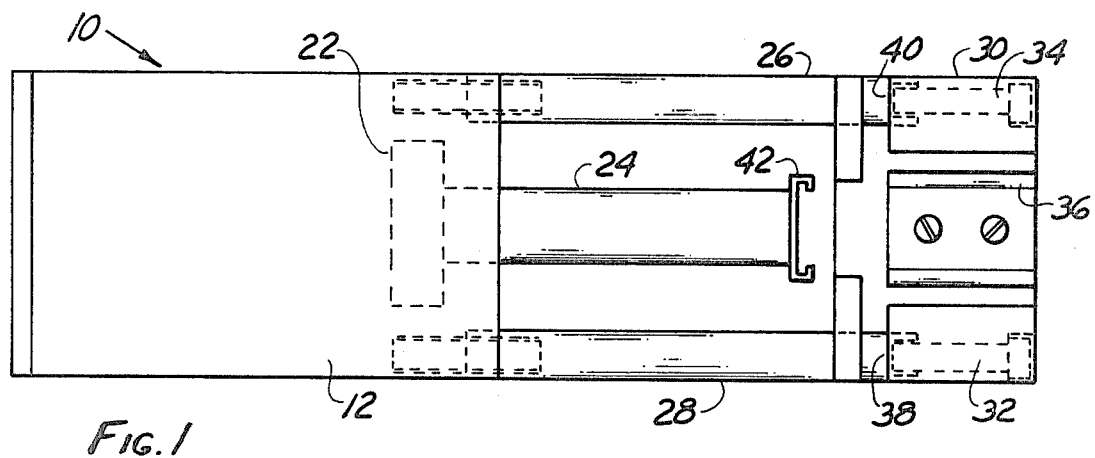
FIG. 1 is a top plan view of the thermodilution injector of the present invention.
Figure 2:
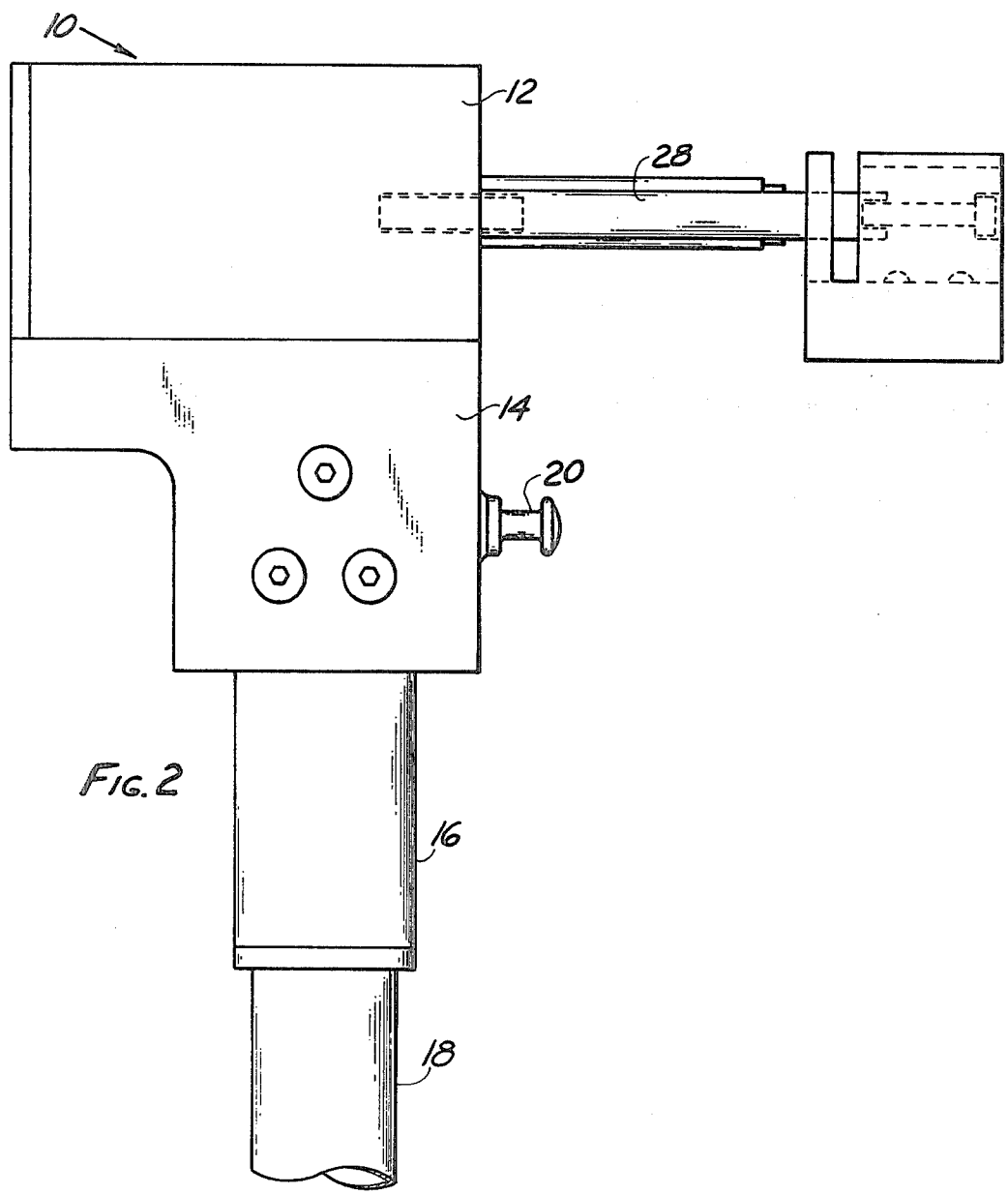
FIG. 2 is a side elevation view of the thermodilution injector of the present invention.

Turning now to a combined consideration of FIGS. 1, 2 and 3, the thermodilution injector, indicated generally at 10, has an upper enclosed body portion 12 of generally cylindrical shape which houses the actuating piston, a lower body portion 14 which serves as the handle, and a lower cylindrical projection made up of an upper section 16 and a lower section 18 removably fastened to section 16. The upper portion 16 of the cylindrical projection houses a flow regulator, and the lower section 18 houses a pressurized gas supply for the injector. An actuating trigger 20 projects from handle section 14, trigger 20 being the plunger of a double detent two position flow control valve. Upper body 12 serves as the cylinder for an actuating piston 22 (shown in phantom in FIG. 1) which has a rod 24 which projects outwardly toward the front of the injector. As will be described in more detail hereinafter, rod 24 actuates the plunger of a syringe for the delivery of injectate.

A pair of support arms 26 and 28 project from the front of upper body 12, the support arms being screw fastened to the front of upper body 12. A syringe holder 30 is mounted on the ends of support arms 26 and 28 by elongated screws 32 and 34. Syringe holder 30 has a centrally located retaining clip 36 which is generally U-shaped in configuration, with the legs of the U having arcuate sides to receive a syringe (see FIG. 3). Retaining clip 36 is of spring metal and it is sized to receive and grip a standard medical syringe. Slots 38 and 40 are formed in the sides of holder 30 to extend over each of the support arms 26 and 28, the slots 38 and 40 serving to receive the wings of a syringe body. Thus, it will be seen that a syringe can be securely held in holder 30 by inserting the syringe into the top of clip 36, the sides of clip 36 deflecting outward to receive the syringe and then returning to the unflexed position to hold the body of the syringe. At the same time, the wings normally present on a standard syringe are inserted in slots 38 and 40 so that the syringe is fixed against axial movement.

An adapter element 42 is fastened to the end of piston rod 24, the adapter element having a slotted head to receive the thumb button on the end of a syringe plunger so that the syringe plunger is connected to rod 24 and will be moved in and out of the syringe in accordance with the motion of rod 24.

When a syringe is appropriately located in holder 30 with the thumb button of the plunger in adapter 42, the plunger is moved forward to deliver injectate or withdrawn to aspirate a new load of injectate into the syringe in accordance with the movement of piston 22 and rod 24. The piston is powered by a pressurized gas supply, such as a $CO_2$ cartridge housed in projection 18, the delivery pressure being regulated by a pressure regulator in projection 16.

Referring to FIG. 4, a schematic diagram is shown of the pneumatic system. The pressurized gas from projection 18 passes through a pressure regulating valve 44 and is delivered to a manually operated two position valve 46 which is operated by a trigger 20. Valve 46 is a four-way two position valve which is detented to hold the valve in either of the two positions in which it is set by movement of trigger 20. Valve 46 may be Humphrey Model 41PPX obtainable from Humphrey Products, Division of General Gas Light Company, Kalamazoo, Michigan. In the position shown in FIG. 4, valve 46 would be delivering pressurized gas to the left side of piston 22, and the right side of piston 22 would be vented to atmosphere through a restriction 48. In this position of the valve, piston 22 would be moving rearwardly to withdraw the plunger from the syringe to aspirate the syringe. In the other position of valve 46, pressurized gas would be delivered to the right side of piston 22, and the left side of piston 22 would be vented directly to atmosphere so that piston 22 would move in the direction to push the plunger into the body of the syringe to deliver injectate. The presence of restriction 48 provides for a two speed operation of piston 22. The speed at which the piston will move rearwardly, and hence withdraw the plunger for aspiration, will be less than the forward motion of the piston and plunger because of the effect of restriction 48. Thus, piston 22, rod 24 and the plunger of the syringe will move forward at a first speed to deliver injectate and will move in the reverse direction at a second and slower speed appropriate for aspiration for another round of injection. It is extremely important to note that the forward motion of piston 22, rod 24 and the plunger of the syringe will always be at a constant speed, repeatable for each cycle of injection, because of the constant operating pressure which is always present on the right side of piston 22 when the piston is being driven forward. Thus, the injectate is always delivered at a constant flow rate and the elapsed time for injection will always be the same for each cycle of injection. Thus, the serious problems of inaccuracy heretofore present in delivering the injectate are totally eliminated in the present invention.

In the operation of the thermodilution injector of the present invention, trigger 20 would be first pulled outwardly relative to the body of the injector, this outward position being the aspiration position as shown in FIG. 4. Lower projection 18 would then be unscrewed from upper projection 16, and a $CO_2$ cartridge 50 (shown in phantom in FIG. 3) is inserted, neck up, in projection 18. Lower projection 18 is then rejoined to upper projection 16 so that the sealed end of the $CO_2$ cartridge is pierced by a pin extending downwardly from projection 16 in the known manner to permit flow of the pressurized gas supply of the $CO_2$ cartridge. If it is desired to test the device for pressure at this point, trigger 20 can be pushed inwardly to its inner detent position and then pulled outwardly to its outer detent position which will cause a cycling of piston 22 and rod 24. Next, a syringe is positioned in holder 30, with the body of the syringe being held by grip 36, the wings of the syringe being held in slots 38 and 40 and the head of the syringe being positioned in the slot of rod adapter 42. It should be noted that the capacity of various syringe models for a given stroke will vary, so a syringe should be selected to provide the desired volume of injectate for the stroke of the unit. Preferably, the syringe should be connected to the catheter before insertion in holder 30, and the syringe should be filled with the desired volume of injectate before being positioned in the holder. When the patient is ready and all of the other monitoring instruments have been prepared for measuring cardiac output, and the signal is given from the attending physician to inject the injectate, the operator of the unit of the present invention will then merely squeeze trigger 20 rapidly and firmly to move trigger 20 to its inner detent position. This movement of trigger 20 will switch valve 46 to the second position shown in FIG. 4 whereby piston 22, rod 24 and the plunger of the syringe will advance and inject the entire contents of the syringe in a predetermined period of time, such as on the order of two seconds. To refill the syringe, the syringe is merely connected to a reservoir of injectate in any known and desired manner, and trigger 20 is then pulled outwardly to its outer detent position. Valve 46 will then be switched to the position shown in FIG. 4 whereby piston 22 and rod 24 and the plunger of the syringe will be withdrawn (at a slower speed than the advance) to aspirate a constant volume of injectate in a desired time period, such as eight seconds. The syringe would then be disconnected from the reservoir and would be ready for another round of injection or injectate at the constant injection volume, injection rate and injection time of the present invention.

When $CO_2$ cartridge 50 is empty, the injection speed of the device will rapidly deteriorate. All that then needs to be done is to replace the empty $CO_2$ cartridge with a fully charged $CO_2$ cartridge, and operation of the system can continue.

If it is desired to inject less than the total capacity of the syringe, the syringe should be filled in each aspiration to the desired smaller volume and placed in holder 30 as previously described. However, the thumb button on the plunger should be connected into the retaining slot in rod adapter 42. In this configuration, the piston rod 24 will advance freely until it strikes the retracted syringe plunger, and the volume of injectate will then be delivered. Repeated operation in this mode requires manual aspiration of the syringe.

Referring now to FIGS. 5 and 6, a modified version of the thermodilution injector is shown which incorporates a first very important feature of variable injection rate and a second very important feature relating to safety which prevents inadvertent aspiration. FIG. 5 shows a modified version of the body portion of the injector of FIG. 1, and FIG. 6 shows the schematic of the pneumatic circuit for this modified version. In the modified version of FIG. 5, a four way control valve is housed in section 100 of the housing. The four way valve is indicated at 102 in FIG. 6, and it includes a push button 104 to operate the valve and a spring 106 to urge and return the valve to its unoperated or off position. Section 108 of the housing contains a variable pressure regulator valve 110 which is operated by a push button 112 against a return spring 114 to vary the pressure drop across the regulator depending on the amount of depression of button 112. As can best be seen in FIG. 6, the configuration of FIGS. 5 and 6 incorporates four way spring return valve 102 and variable pressure regulator 110 in the line between pressure regulator 44 and piston cylinder 12.

In the embodiment of FIGS. 5 and 6, pressure regulator 44 functions to maintain a constant level of gas pressure as in the FIG. 1 embodiment. However, variable pressure regulator 110 will vary the pressure level of the gas delivered from pressure regulator 44 to piston cylinder 12 to vary the rate of either forward or return motion of piston 12. Thus, the rate of movement of piston 12, either in the delivery or aspirating directions, can be selected and varied by the operator of the device by varying the depression of button 112.

Four way valve 102 determines the direction in which the piston 22 will move, i.e. to the left to deliver injectate, or to the right to aspirate. In the position shown in FIG. 6, which is the normal or unactuated position of valve 102, the valve is positioned to deliver pressurized fluid to the right of piston 22 and vent the left side of piston 22 which would drive the piston to the left to operate the syringe to deliver injectate. When button 104 is depressed to move valve 102 to its second position, the valve is positioned to deliver pressurized fluid to the left side of piston 22 while the right side of piston 22 is vented, which would drive piston 22 to the right to aspirate the syringe. However, no pressurized fluid is delivered to valve 102 until variable pressure regulator 110 is operated.

Spring 106 will retain valve 102 in the position shown in FIG. 6 unless the operator depresses button 104 to move the valve to the second position; and spring 106 will return valve 104 to the position shown in FIG. 6 whenever the operating force is removed from button 104. Thus, it will be seen that the position of valve 102 determines the direction of movement of piston 22 and determines whether the device will operate in the mode to deliver injectate or to aspirate, while the position of button 112 to vary the setting of variable regulator 110 will determine the rate of movement of piston 22 and hence the rate of movement of syringe plunger in either the injectate delivery direction or the aspiration direction. In addition, it will also be recognized that since the normal position of valve 102 is to effect delivery of injectate, aspiration can only be effected by deliberate depression of button 104 by the operator. Accordingly, inadvertent or accidental aspiration is avoided, since aspiration requires the deliberate depression of both buttons 104 and 112.

Figure 7:
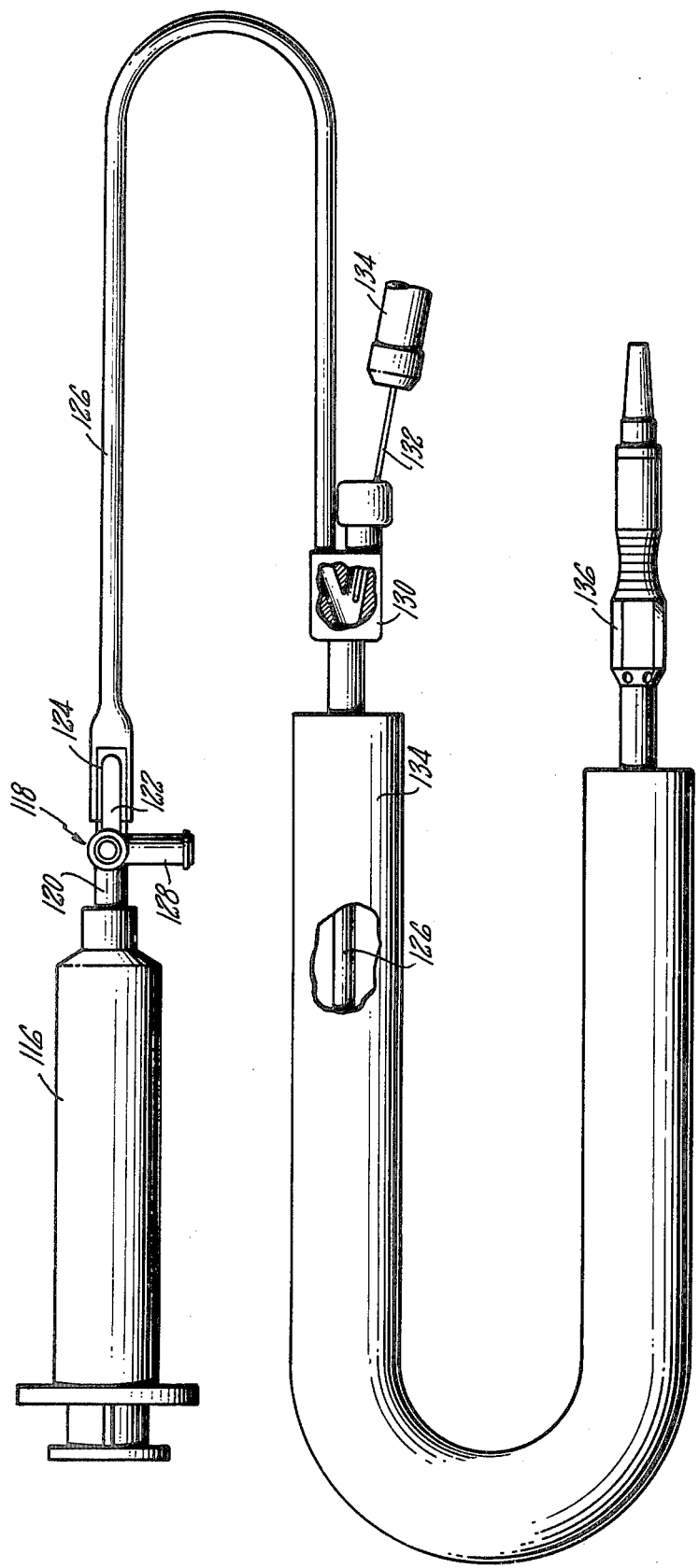
FIG. 7 shows a bolus injection set for use with an injector for purposes of isotope injection.

Referring now to FIGS. 7 and 8, still another modification is shown wherein the injection apparatus can be used as a bolus injector, particularly in the nuclear medicine field for isotope injection. FIG. 7 shows a bolus injection set, while FIG. 8 shows the schematic diagram of the pneumatic circuit for actuating the injector when used as a bolus injector. A standard syringe 116 is mounted in the injector apparatus as described above with respect to FIG. 1. Syringe 116 is fitted with a three way syringe set 118 which has one channel 120 communicating with the syringe, a second channel 124 which communicates with an output line 126 and a third conduit 128 which communicates with a fluid reservoir. Three way set 118 has an exterior handle 122 which positions an internal stop cock valve in three way set 118, the internal valve being configured to have three positions where (1) conduit 120 comunicates with conduit 124 to deliver the contents of the syringe to output line 126 while preventing any communication with conduit 128, (2) a second position in which conduit 120 is connected to conduit 128 to permit aspiration of fluid from a reservoir to load syringe 116 while preventing any communication with output conduit 124, and (3) a third position in which conduit 128 is connected to conduit 124 to flush the output line or administer intravenous fluids.

Output line 126 contains a "Y" type injection site 130 which receives a needle 132 from a syringe or other injection mechanism 134 to inject material from the syringe 134 to mix with the contents of line 126. In the preferred configuration of an isotope injector, syringe 116 and line 126 are filled with an injectate such as a saline solution, and injector 134 supplies a radioactive isotope to be carried in the saline solution in output line 126. The portion of output line 126 downstream of injection site 130 is encased in a lead or other suitable shield 134 to protect against radiation. Conduit 126 terminates in a adapter 136 which is connected to conduit 126 at the downstream end of shield 134, and an injection needle or a catheter would be positioned at the downstream end of adapter 136 for injection of the isotope into a patient for examination purposes.

In the operation of the device shown in FIG. 7, saline solution would be manually aspirated from the reservoir into syringe 116 and then delivered to output line 126 and needle adapter 136 to completely fill output line 126, adapter 136 and the injection needle or catheter attached to adapter 136, and a full charge of saline solution would be stored in syringe 116. After the syringe, output line and adapter (and needle or catheter) are charged with saline solution, a precisely measured volume of a radioactive isotope is injected at Y site 130. The volume of isotope injected may be any measured amount up to the total volume contained in that portion of output line 126 which is shielded by shield 134. Whatever selected amount of isotope is injected will, of course, displace and eject a corresponding volume of saline solution through adapter 136. The bolus injector set is then fully charged and ready for operation. Bearing in mind that syringe 116 is mounted in an injector 10, operation of the bolus isotope injection set is effected by cycling the injector to drive the plunger of syringe 116 forward to deliver the isotope and saline solution to the patient. It is most important to note that the entire isotope solution stored in the portion of line 126 shielded by shield 134 is delivered to the patient as a discrete bolus flushed with the solution in syringe 116 and line 126. To effect bolus injection, the aspirated volume of syringe 116 must be equal to or greater than the volume of line 126 encased in shield 134.

FIG. 8 shows a schematic of the pneumatic circuit for injector 10 when used as an isotope injector. A spring loaded two position four way valve 138 is positioned between pressure regulator 44 and cylinder 12. Valve 138 is urged to a first or non-operating position by a return spring 140, and the valve has a push button 142 to operate the valve. Valve 138 would be housed in the injector in the position such as valve 100, with actuating button 142 projecting similarly to actuating button 104. In the first or unactuated position of valve 138, both the right and left sides of piston 22 are vented to atmosphere, and the supply line from pressure regulator 144 is dead ended at the valve. That state of the valve is shown in FIG. 8. When button 142 is depressed to actuate the isotope injector, the valve moves to its second position where pressurized fluid is delivered to the right side of piston 22 while the left side of piston 22 is vented, thus causing piston 22 to move to the left to push the plunger of the syringe for injection. The operator of the injector retains control over injection during the entire injection stroke. If the operator releases the actuating pressure from button 142, spring 140 will automatically return the valve 138 to its unoperated position whereby both sides of piston 22 will be vented and the injection stroke will cease. Thus, an important safety feature is incorporated in the device in that the operator must consciously maintain the actuating force on button 142 to complete the injection, and the injection will be automatically terminated at any intermediate point upon removal of the operating force from button 142. Aspiration and return of piston 22 to the right are accomplished manually.

While a preferred embodiment has been shown and described, various modifications and substitutions may be made thereto without departing from the spirit and scope of the invention. Accordingly, it will be understood that the present invention has been described by way of illustration and not limitation.

What is claimed is:

1. An injector for delivering injectate to a patient including:
    a body;
    support means on said body for receiving a syringe;
    actuator means in said body responsive to pressurized fluid to actuate said syringe, said actuator means having a movable output member;
    connecting means for connecting said actuator means output member to a syringe in said support means;
    a source of pressurized fluid for said actuator means, said source of pressurized fluid being internally contained in said body;
    regulating means in said body for maintaining at a substantially constant level the pressure of pressurized fluid delivered from said pressurized fluid source in said body to said actuator means whereby said actuator means output member will move at a substantially constant rate; and
    control means in said body for controlling delivery of the pressurized fluid to said actuator means.

2. An injector as in claim 1 wherein:
    said control means selectively communicates with said actuator means to deliver pressurized fluid to operate said actuator means in forward and reverse directions.

3. An injector as in claim 2 including:
    means to reduce the rate of travel of said actuator means in the reverse direction below the rate of travel in the forward direction.

4. An injector as in claim 1 wherein said control means includes:
    two position four way valve means with detent means to hold the valve means in either of the two positions.

5. A thermodilution injector for delivering injectate to a patient including:
    a body;
    support means on said body for receiving a syringe;
    actuator means in said body responsive to pressurized fluid to actuate said syringe;
    connecting means for connecting said actuator means to a syringe in said support means;
    a source of pressurized fluid in said body for said actuator means;
    first regulating means in said body for regulating the pressure of pressurized fluid delivered to said actuator means;
    second regulating means in said body for varying the pressure of pressurized fluid delivered to said actuator means; and
    control means for controlling the delivery of pressurized fluid to said actuator means;
    said control means being normally in a first position to deliver pressurized fluid to drive said actuator means in a first direction and being movable by an actuating signal to a second position to drive said actuator means in a second direction, said control means returning to said first position upon cessation of the actuating signal.

6. A thermodilution injector as in claim 5 wherein:
    said second regulating means has an unactuated position to terminate flow of pressurized fluid to said actuator means and is adjustable from said normal position by an actuating signal, said second regulating means returning to said unactuated position upon cessation of said actuating signal.

7. A thermodilution injector as in claim 6 wherein:
    said second regulating means is between said first regulating means and said control means.

8. A thermodilution injector as in claim 6 wherein:
    said control means is spring loaded toward said first position; and
    said second regulating means is spring loaded toward said unactuated position.

9. A thermodilution injector as in claim 8 wherein:

said first regulating means is a pressure regulator having a desired output pressure; and said second regulating means is a variable pressure regulator having a variable output pressure.

10. An injector for delivering injectate to a patient including:

a body;

support means on said body for receiving a syringe;

actuator means in said body responsive to pressurized fluid to actuate said syringe;

connecting means for connecting said actuator means to a syringe in said support means;

a source of pressurized fluid for said actuator means;

regulating means for regulating the pressure of pressurized fluid delivered to said actuator means;

control means for controlling delivery of the pressurized fluid to said actuator means;

a delivery line connected to said syringe;

radioactive shield means protecting part of said delivery line; and injection site means connected to said delivery line to introduce radioactive material to said part of said delivery line protected by said shield.

11. An injector as in claim 10 wherein:

said injection site means is upstream of said shield in the direction of flow through said delivery line.

12. An injector as in claim 11 wherein:

said injection site means is a Y injection site.

13. An injector as in claim 10 wherein:

said control means is normally urged to a first position to prevent the flow of pressurized fluid to said actuator means and vent said actuator means; and said control means is movable from said first position upon receipt of an actuating signal to deliver pressurized fluid to said actuator means to deliver said radioactive material in a discrete bolus to a patient.

14. An injection set for delivering injectate to a patient including:

a delivery line for injectate, said delivery line being connectable to a supply of fluid and to a fluid injecting device;

radioactive shield means protecting part of said delivery line; and injection site means connected to said delivery line to introduce radioactive material to said part of said delivery line protected by said shield.

15. An injector set as in claim 14 wherein:

said injector site means is upstream of said shield in the direction of flow through said delivery line.

16. An injector set as in claim 15 wherein:

said injection site means is a Y injection site.

17. An injector for delivering injectate to a patient including:

a body;

support means on said body for receiving a syringe;

bidirectional actuator means in said body movable in forward and reverse directions in response to pressurized fluid to actuate said syringe;

connecting means for connecting said actuator means to a syringe in said support means;

a source of pressurized fluid for said actuating means;

regulating means in said body for regulating the pressure of pressurized fluid delivered to said actuator means;

control means in said body for controlling delivery of the pressurized fluid to said actuator means to determine the direction of movement of said actuator means; and means to reduce the rate of travel of said actuator means in one direction below the rate of travel in the other direction.

18. An injector as in claim 17 wherein said one direction is the reverse direction commensurate with aspiration of a syringe and said other direction is the forward direction to operate a syringe for delivery of fluid therein.

19. An injector as in claim 17 wherein said control means includes:

two position four way valve means with detent means to hold the valve means in either of the two positions.

20. An injector as in claim 17 wherein said connecting means includes:

a pair of spaced apart arms extending from said body;

a syringe holder connected to said spaced apart arms; and retainer means on said holder for retaining a syringe in fixed position relative to said holder.

21. An injector as in claim 20 wherein:

said actuator means is a piston having a rod extending out of said body toward said holder; and said connecting means is an adapter on the end of said rod shaped to receive and engage the end of a syringe plunger.

22. An injector for delivering injectate to a patient including:

a body;

a pair of spaced apart arms extending from said body;

a syringe holder connected to said spaced apart arms;

retainer means on said holder for retaining a syringe in fixed position relative to said holder;

movable actuator means in said body, said actuator means being responsive to pressurized fluid;

means for connecting said actuator means to a syringe in said holder whereby said actuator means will operate the syringe;

a source of pressurized fluid for said actuator means, said source of pressurized fluid being internally contained in said body;

regulating means in said body for regulating the pressure of pressurized fluid delivered from said pressurized fluid source in said body to said actuator means; and control means in said body for controlling delivery of the pressurized fluid to said actuator means.

23. An injector as in claim 22 wherein:

said actuator means is a piston having a rod extending out of said body toward said holder; and said connecting means is an adapter on the end of said rod shaped to receive and engage the end of a syringe plunger.

* * * * *